(12) United States Patent
Saber

(10) Patent No.: US 11,344,651 B2
(45) Date of Patent: *May 31, 2022

(54) KITS, COMPOSITIONS AND METHODS FOR WOUND TREATMENT AND MANAGEMENT

(71) Applicant: Shienlin Saber, Laguna Beach, CA (US)

(72) Inventor: Shienlin Saber, Laguna Beach, CA (US)

(73) Assignee: DIRECT COMPONENTS INC., Cheyenne, WY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/823,250

(22) Filed: Mar. 18, 2020

(65) Prior Publication Data

US 2020/0215224 A1  Jul. 9, 2020

Related U.S. Application Data

(63) Continuation of application No. 15/703,262, filed on Sep. 13, 2017, now Pat. No. 10,660,985.

(60) Provisional application No. 62/394,700, filed on Sep. 14, 2016.

(51) Int. Cl.
  *A61K 47/30* (2006.01)
  *A61L 15/16* (2006.01)
  *A61L 26/00* (2006.01)

(52) U.S. Cl.
  CPC ....... *A61L 26/0019* (2013.01); *A61L 26/0052* (2013.01); *A61L 26/0066* (2013.01); *A61L 2300/402* (2013.01); *A61L 2300/404* (2013.01); *A61L 2300/406* (2013.01); *A61L 2300/412* (2013.01); *A61L 2300/418* (2013.01); *A61L 2300/424* (2013.01)

(58) Field of Classification Search
  CPC ............................. A61K 9/7015; A61K 8/895
  USPC ............................. 514/772.3; 424/445, 447
  See application file for complete search history.

(56) References Cited

U.S. PATENT DOCUMENTS 10,660,985 B2 *  5/2020  Saber ................. A61L 26/0052

OTHER PUBLICATIONS

Santoro et al. " Vascular access for hemodialysis: current perspectives," International J. Nephrology and Renovascular Disease, 2014, vol. 7, pp. 281-294. (Year: 2014).*

* cited by examiner

*Primary Examiner* — Shengjun Wang
(74) *Attorney, Agent, or Firm* — SoCal IP Law Group LLP; Steven C. Sereboff; Brian S. Tamsut

(57) ABSTRACT

The inventive subject matter provides compositions and methods for transiently or permanently treating or managing an injury. Contemplated compositions are polymerizable in situ over short time periods, even in the presence of blood, without undue exothermic heat. Contemplated compositions may further comprise an anesthetic, an antiseptic, an adhesion promoter, and/or a vasoconstrictor.

20 Claims, 8 Drawing Sheets

KITS, COMPOSITIONS AND METHODS FOR WOUND TREATMENT AND MANAGEMENT

CROSS REFERENCE TO RELATED APPLICATION

This application is a continuation of U.S. application Ser. No. 15/703,262, filed Sep. 13, 2017, which claims the benefit of U.S. Provisional Application Ser. No. 62/394,700 filed Sep. 14, 2016, the entire disclosures of each are incorporated herein by reference.

FIELD OF THE INVENTION

The field of the invention is wound treatment, especially transitory wound treatment kits, and compositions and methods therefor.

BACKGROUND

The background description includes information that may be useful in understanding the present invention. It is not an admission that any of the information provided herein is prior art or relevant to the presently claimed invention, or that any publication specifically or implicitly referenced is prior art.

Many people work in high-risk fields where traumatic injuries resulting in severe bleeding, burns, or tissue damage are likely to occur. Such people include athletes, stuntmen, military servicemen, medical professionals, police officers, firefighters, construction workers, iron and steel workers, and veterinary service professionals. Even those who do not work in high-risk fields sporadically find themselves in situations where it is necessary to clean a wound, stop a bleed, or manage pain, although further treatment at a clinic or hospital is often required or recommended.

Existing options for non-medical professionals temporarily or otherwise treating minor injuries include Dermoplast™ pain relieving and antibacterial sprays, Bactine™ pain relieving cleansing spray, and Medique™ topical wound care line of products. However, such options are formulated for external/topical use, and do not appear to be appropriate for use to stop a bleed where there is a severe injury, such as a stab wound, laceration, amputation, or gun shot wound.

For more serious injuries, non-medical professionals often attempt to apply a tourniquet or a constant, direct pressure with layers of gauze or cloth. They may also attempt to clean the wound with alcohol or peroxide, apply an antibiotic ointment, or apply bandages to the skin outside the wound as a placeholder until the patient can be seen by a medical professional.

Unfortunately, existing emergency treatment options suffer from various disadvantages, such as the inability to effectively stop the bleed, inability to at least temporarily relieve pain, and inability to seal a wound from infection or further bleeding without a third party applying a constant, direct pressure on the injury. Additionally, many non-medical professionals are not aware of the steps necessary to properly treat or manage a wound, which can be numerous and risky. Moreover, and especially where gauze or other materials were used to attempt to seal a wound, removal often adds further traumatic injury, especially where the material has been in contact with the wound for longer periods of time (e.g., several hours or days).

Certain sealing compositions are known in the art, although they are applicable and used in very different contexts. For example, US 2008/0226577 to L'Alloret et al. and U.S. Pat. No. 8,691,202 to Yu et al. teach cosmetic kits for topical use, wherein separately packaged compositions form a thin film to hide wrinkles and other skin imperfections. However, the compositions of L'Alloret and Yu are not suitable for treatment of a wound or placement within a body cavity, and there does not appear to be any indication that such compositions would even form a film in the presence of blood or tissue. These and all other extrinsic references are incorporated herein by reference in their entirety. Where a definition or use of a term in an incorporated reference is inconsistent or contrary to the definition of that term provided herein, the definition of that term provided herein applies and the definition of that term in the reference does not apply.

As another example, LeGoo™, a poloxamer gel with reverse thermosensitive properties, is a biopolymer gel that allows surgeons to temporarily stop blood flow in a vessel during surgery without the use of a clamp or other conventional occlusion device (see e.g., Ann Thorac Surg. 2011 December; 92(6):2235-9). LeGoo is a liquid gel at colder temperature, and forms a plug when injected into a blood vessel. The plug dissolves via cooling or spontaneously after only several minutes, and cannot subsequently reform. LeGoo is not intended to be removed as a solid, and is only marketed for temporary endovascular occlusion of blood vessels up to 4 mm in diameter—not treatment or management of open wounds (e.g., wounds involving a break in skin, typically accompanied with bleeding). While LeGoo undergoes a temperature-induced phase change, there is no alteration in the product's chemical composition, and the material does not cure in situ. Consequently, LeGoo is not suitable for treatment of traumatic injury and is also not amenable for use over extended periods of time (e.g., more than 15-30 minutes, or hours). Furthermore, the FDA limits the sale of LeGoo to (or on the order of) physicians. Therefore, such gel would not be suitable for use by a non-medical professional.

Still other hemostatic compositions are known that are based on zeolite (e.g., QuikClot, Z-MEDICA, LLC, 4 Fairfield Blvd., Wallingford, Conn. USA 06492), collagen (Surgicel, Ethicon, US), or starch (TraumaDEX; Medafor, Inc., Minneapolis, Minn. 55430). While zeolite based hemostatic agents are often rapid in action, extreme caution must be taken as severe burns may develop due to exothermic reaction o the zeolite. Moreover, zeolites do not stabilize a would and motion of the injured can trigger reopening of the wound. Similarly, collagen and starch based compositions fail to physically stabilize a wound and are typically not suitable for more serious injuries such as lacerations, stab- or gunshot wounds, or amputations. Moreover, most of these compositions require complete removal prior to further treatment of the injury, which typically retraumatizes a patient.

Thus, while numerous compounds and compositions for wound treatment are known in the art, there is still a need for improved kits, compositions, and methods that will rapidly stop blood loss, even in large injuries, that will stabilize a trauma site, and that is easily removable from the site without retraumatizing a patient. In addition, there is also a need for wound treatments that can remain in place for an extended period, and that can be readily removed by a medical professional without re-injury of the patient.

SUMMARY OF THE INVENTION

The inventive subject matter is directed to kits, compounds, compositions, and methods for simply and effectively treating and managing a wide range of injuries, including injuries that result in broken skin, bleeding, tissue damage, or any combination thereof. Compounds and methods presented herein will allow for rapidly stopping blood loss, even in large injuries, will stabilize a trauma site, and are easily removable from the site without retraumatizing a patient (e.g., seal can be removed without tearing tissue from wound margins or without requiring cutting seal away from wound margins). In addition, contemplated wound treatments can remain in place for an extended period, and can be readily removed without re-injury of the patient. Therefore, the kits, compositions, and methods presented herein can be used for transitory treatment and management of an injury until the injured is able to be cared for by a medical professional, or can even be used as the sole or primary treatment for a wound (e.g., minor wound).

In one aspect of the inventive subject matter, contemplated methods for treating an injury can comprise applying a polymerizable composition into and/or over the injury to form a seal, wherein the seal can subsequently be removed for further treatment of the wound. A base component could be applied to the injury, prior to or contemporaneously with application of the polymerizable composition, and such base component could comprise a primer. The base component, the polymerizable composition, or both can optionally include one or more of an anesthetic, an antiseptic, an adhesion promoter, a botanical (e.g., chamomile, marigold, arnica), a drug, a UV absorbing agent to prevent sunburn, a vitamin (e.g., ascorbic acid, retinol, niacinamide), an antipruritic, a catalyst, a haemostatic agent, a compound that is detectable with medial imaging devices, a colorant, and a vasoconstrictor. When included in the base component or the polymerizable composition, the additional ingredients will in some preferred aspects not be present in an amount that significantly prolongs cure time of the polymerizable composition, alters mechanical properties, and/or decreases adhesion strength of the seal.

Contemplated polymerizable compositions, upon forming a seal in situ, will preferably be elastic or semi-elastic. For example, some contemplated compositions will have an elasticity at break of at least 200%, more preferably at least 300%, and more preferably at least 400% (e.g., between 200-1000%, between 400 and 800%, between 450-600%), to allow for movement and stretching of the body without compromising the seal. Likewise, contemplated compounds and compositions will be deformable upon compression (e.g., using moderate manual force or force common with wound compression upon motion of a body part having the wound). Where the polymerizable compositions are used in different applications, or in areas of skin that do not require significant elasticity, it is contemplated that the polymerizable composition can have a lower elasticity at break, or even be inelastic or substantially inelastic, or comprise a splint. Additionally, some preferred polymerizable compositions will have a hardness sufficient to prevent unwanted flowing of the seal. For example, some contemplated seals will have a hardness of at least 10 on the Shore 00 durometer scale, and more preferably at least 10 on the Shore A scale.

Some contemplated polymerizable compositions are advantageously capable of forming the seal even in the presence of blood or animal tissue. Applicant has surprisingly discovered that the presence of blood could in fact improve (e.g., accelerate) a cure time of the polymerizable composition. For example, where some contemplated formulations were placed on an injury where blood was exposed, the cure time was found to decrease by about 15 seconds. Without wishing to be bound by any particular theory, the Applicant contemplates that one or more compounds in blood (e.g., heme or ionic iron in blood) may speed up the cure time of the polymerizable formulation. Moreover, it was observed that polymerization of the compounds to form a seal was also accelerated at body temperature (relative to ambient, 20 degree C. temperature cure), which is especially desirable for treatment of trauma with significant blood loss. Additionally, the polymerizable composition has been found to infuse, while being flowable, approximately 0.25 mm-5 mm into surrounding tissue and blood vessels, thereby providing a secure seal in and around the wound without causing an embolus. Most notably, upon curing, contemplated compounds and compositions were not only sufficiently flexible to remain in the site of trauma even when the site of injury was exposed to compression and stretching, but could be removed intact from the site of trauma without causing further injury.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
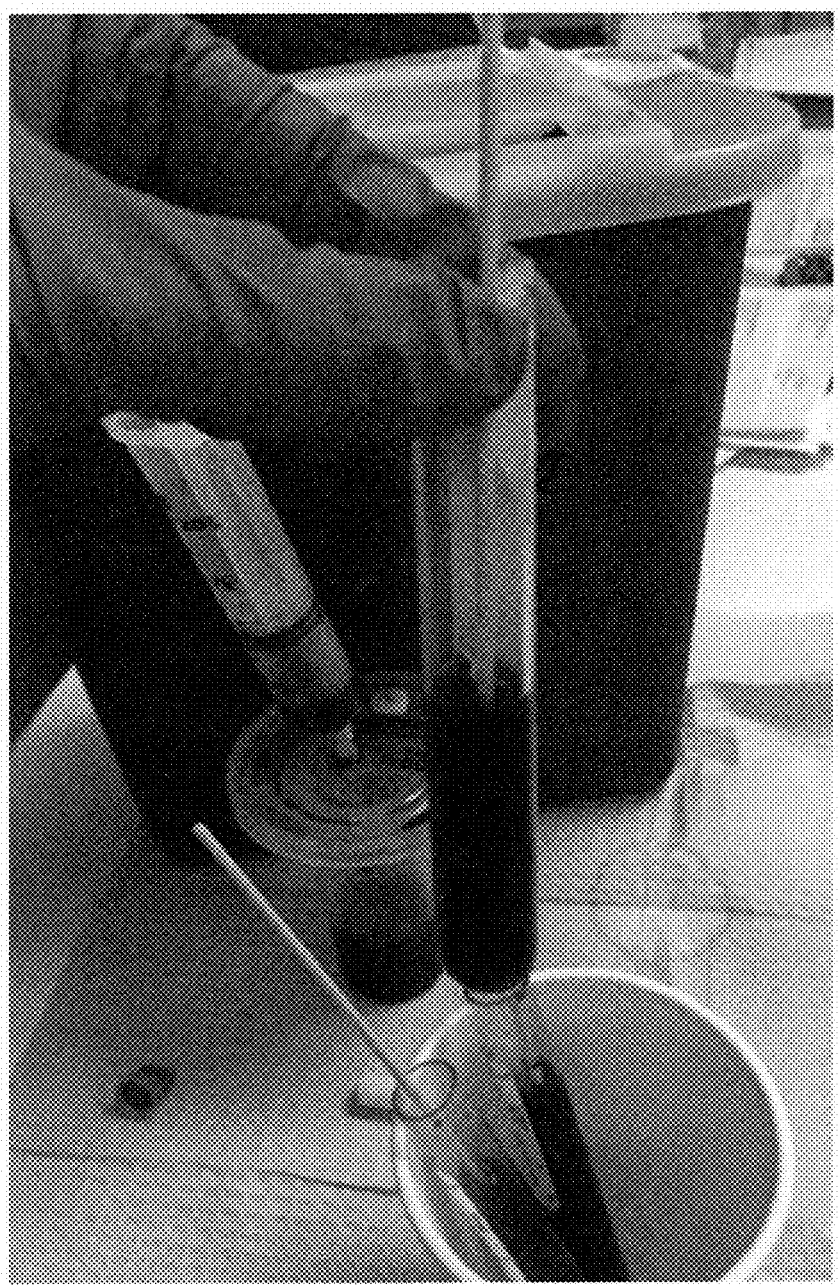
FIG. 1 illustrates a polymerizable formulation placed within platelet-rich plasma in a vacutainer.
Figure 2A:
FIGS. 2A-2B illustrate the polymerizable formulations after they have cured and have been removed from the vacutainers.
Figure 2B:

The inventive subject matter provides compositions and methods for treating an injury by forming secure seal using a composition that polymerizes in situ within and/or around a wound. Such seal can be formed from any polymerizable or cross linkable composition to generate a barrier on the substrate it is attached to, especially skin, exposed tissue, open wounds, cuts, and burns. Contemplated seals can act as a barrier to completely or substantially completely block the substrate from exposure to the environment (e.g., water, dirt, sun/radiation exposure, etc.). Additionally or alternatively, contemplated seals can stop a bleed and remain adhered to surrounding skin or tissue for a period of at least 1 hour (e.g., at least 3 hours, at least 5 hours, at least 8 hours, at least 10 hours, at least 12 hours, at least 15 hours, at least 20 hours, at least 1 day, at least 2 days, at least 3 days, at least 4 days, at least 5 days, at least 10 days, at least 20 days, or up to 29 days, and even longer). Viewed from a different perspective, it is contemplated that a seal formed on at least one of skin and an open wound can be configured to remain substantially adhered to the substrate (e.g., at least 80% of the seal remains adhered to the skin, at least 90% of the seal remains adhered to the skin, at least 95% of the seal remains adhered to the skin, 100% of the seal remains adhered to the skin) for a period of at least one hour (e.g., at least 2 hours, at least 3 hours, at least 6 hours), even .under water, or a period of at least 1 day (e.g., at least 2 days, at least 3 days, at least 4 days, at least 5 days). Viewed from yet another perspective, contemplated seals can stop a bleed within 5 minutes, more preferably within 2 minutes or within 1 minute, and can prevent a rebleed for a period of at least 1 hour, more preferably at least 12 hours, and even more preferably at least 24 hours or at least 48 hours.

In addition, the inventor also discovered that the polymer, when cured, had sufficient tensile strength and elasticity to allow suturing the cured polymer to skin, which can further stabilize the temporary wound cover, especially where there is an expected delay between covering the wound and subsequent treatment, and/or where movement or placement of the polymerized composition will likely result in at least partial dislodgment of the cured polymer.

Furthermore, contemplated seals can be removed, typically intact, from the skin and/or wound without further injury to the skin or wound. Such advantage is especially desirable as removal of other hemostatic compositions often results in further tissue damage or requires surgical removal. In contrast, contemplated compositions can be removed from the site of injury without the need of cutting away tissue from the wound margins, or without the polymerized composition tearing away live tissue (as opposed to dead cells or necrotic tissue) from the margins of the wound. Thus, removal of contemplated compositions is possible without re-injury and/or need for cauterization.

It should therefore be appreciated that the seal can be partial or complete with respect to the site of injury, and can be a permanent or temporary, removable seal. It it contemplated that the polymerizable composition could be used for a wide range of injuries, including for example burns, animal or human bite wounds, stings, cuts, scrapes, stab or puncture wounds, gun shot wounds, lacerations, amputations, and any other minor or traumatic injury to any part of a human or other animals. Viewed from a different perspective, it should be recognized that the seal can be formed over a surface of a body (injured or not injured), and even in a body opening or cavity (injured or not). For example, open wounds due to a explosive blast can be covered (and with that bleeding is stopped) by application of the film to the site of injury, while the outer ear canal can be sealed with the compositions to protect the inner ear from injury and sound where the ear drum is perforated.

In further contemplated aspects, the compounds and compositions according to the inventive subject matter can also be applied to necrotic or ulcerated tissue or tissue areas after removal of necrotic, ulcerous, or cancerous tissue to form a protective layer under which remaining tissue can regenerate fresh tissue for wound healing. In such scenario, it should be noted that the compounds and compositions according to the inventive subject matter will not only form a protective seal above the treated area, but also provide a moisture barrier that has been shown to promote wound healing and regeneration of healthy tissue in a remarkable fast and cosmetically attractive manner.

With respect to suitable compounds and compositions it is contemplated that all commercially available and/or custom-formulated polymerizable and/or cross linkable compositions are for use herein, including vinyl-based cure systems, silicone-based cure systems, peroxide-cure systems, heat cure systems, room temperature vulcanizing moisture cure systems, temperature activated systems, photoinitiated cure systems, and addition-cure systems. Additionally, all suitable polymerization reactions are contemplated, including hydrosilylation polymerization, condensation polymerization, and addition (chain-growth) polymerization (e.g., photopolymerization), and radical polymerization. In this context it should be appreciated that cross linking and polymerization can be used interchangeably as both reactions increase the size of a polymeric backbone (and molecular weight) and decrease flowability to a point of cure.

In some preferred aspects, the polymerizable composition will result in a cured seal having sufficient elasticity to allow the user to move around comfortably without dislodging the seal or adding to the pain or discomfort at the injury location. In other preferred aspects, the polymerizable composition can be introduced into a wound and removed without burning or otherwise injuring the tissue. If desired, it is also contemplated that the cured seal can be left in the body, even for extended periods of time, without causing damage to the patient. The polymerizable composition is typically odorless, non-toxic, hypoallergenic, compatible with other treatments, bacteriostatic, non-explosive, non-temperature sensitive, and removable as a single piece, or in sections, after curing.

The polymerizable composition can comprise a one part system, for example, where the polymerizable composition is temperature or light activated. Alternatively, the polymerizable composition can comprise a multi-part system, for example, where a catalyst and a cross-linking component must be kept separate prior to use to prevent premature and undesired curing.

One type of a preferred polymerizable composition comprises a two-part elastomer system that cures at room (20 degree Celsius) or body (37 degree Celsius) temperature and includes (a) a first formulation including a polymer and catalyst (e.g., silicone polymer and platinum or other suitable metal catalyst), and (b) a second formulation comprising a polymer and a crosslinker. One or both of the formulations could include one or more of a filler, a thixotropic agent, an adhesion promoter, and a cure inhibitor to control the cure kinetics.

Where the first and second formulations are separately packaged or contained in a dual chambered system (e.g., a dual chamber syringe that is hermetically closed, or dual chamber flexible pouch with frangible seal between the chambers), cross linking cannot occur until the two components are mixed together (e.g., layered or applied as a mixture).

In some contemplated embodiments, the polymer is a silicone polymer (e.g., siloxane polymer) with a polymer backbone of alternating silicone and oxygen atoms (i.e., siloxane bonds), and hydrocarbon (saturated, unsaturated, aromatic) organic side groups such as methyl, phenyl or vinyl, or a hydrogen attached to the silicon atoms. The siloxane polymer can comprise between 20-100 wt %, more preferably at least 50 wt %, and even more preferably at least 70 wt % (e.g., between 75-85 wt %, between 78-82 wt %) of the polymerizable composition (i.e., of the combined two part formulation where the catalyst and crosslinker are combined).

For example, where polydimethylsiloxane (PDMS) is used, it can be a linear polymer made up of repeating Si—O—Si linkages and a reactive vinyl group on both ends of the polymer chain. There may be organic side groups such as dimethyl bonded to every silicone molecule the backbone of the polymer. Siloxane polymers can also be substituted with diphenyl, methylphenyl, trifluoropropyl, or any combination thereof. Some exemplary siloxanes include oligosiloxanes, polydimethylsiloxane (PDMS), vinyl-endblocked polydiphenyl siloxane, vinyl-endblocked polymethylphenylsiloxane, vinyl-endblocked trifluoropropyl siloxane, vinyl-endblocked polydiethyl siloxane, trimethyl-endblocked methylvinyl polydimethylsiloxane, trimethyl-endblocked methylvinyl polydiphenylsiloxane, trimethyl-endblocked methylvinyl polymethylphenylsiloxane, trimethyl-endblocked methylvinyl polytrifluoropropylsiloxane, and trimethyl-endblocked ethylvinyl polydimethylsiloxane. Contemplated siloxanes can be optically clear, non-toxic and non-flammable.

All suitable chain lengths of the siloxane polymer are contemplated, including between 10-2,500 repeating units long, between 200-1,000 repeating units long, or between 200-400 repeating units long, or between 300-600 repeating units long, or between 300-400 repeating units long (e.g., 340-360), or between 500-800 repeating units long, or between 700-1,000 repeating units long. Thus, siloxane polymers may have an average molecular weight of between about 500-5,000 Daltons, or between about 5,000-20,000 Daltons, or between about 15,000-35,000 Daltons, or between about 35,000-55,000 Daltons, or between about 55,000-100,000 Daltons, or more.

According to another embodiment, a polymer can include a main chain formed primarily of organosiloxane units. Among the silicone compounds contemplated, some may display both curing and adhesive properties, for example depending on the proportion of silicone or whether they are used with a particular additive. It may therefore be possible to adjust the properties of said compositions according to the proposed use.

In some contemplated embodiments where the polymer is a siloxane, the crosslinker is a siloxane crosslinker such as a methyl-hydrogen crosslinker. The crosslinker can comprise between 0.1-50 wt %, between 0.1-10 wt %, and more preferably between 1-5 wt % (e.g., 2 wt %) of the polymerizable composition. An exemplary siloxane crosslinker used in some contemplated compositions is a small chain polymer that is trimethyl endblocked, making the ends of the chain non-functional. All suitable chain lengths of the crosslinker are contemplated, including for example, between 1-100 repeating units, more preferably between 1-50 units, and more preferably between 5-15 units (e.g., 10 units wherein the molecular weight is 800 Daltons).

Along the backbone of the crosslinker can be reactive methyl-hydrogen side groups which can comprise between 1-99 mole %, more preferably between 20-80 mole %, and more preferably between 40-60 mole % (e.g., 50 mole %) of the crosslinker. The remaining mole % can comprise dimethyl side groups. Where each of the methyl-hydrogen side groups and the dimethyl side groups make up approximately 50 mole %, approximately half of the repeating units of the crosslinker will be dimethyl, and approximately half will be methyl hydrogen. Other contemplated crosslinkers include hydride-endblocked polydimethylsiloxane, hydride-endblocked methylhydrogen polysiloxane, trimethyl-endblocked methylhydrogen methylvinyl polysiloxane, trimethyl-endblocked 100 mole % methylhydrogen polysiloxane, hydride-endblocked polydiphenylsiloxane, and hydride-endblocked phenylhydrogen polysiloxane. Although the exemplary crosslinkers described above are siloxane crosslinkers, it should be appreciated that a person skilled in the art would be able to select a suitable crosslinker based on the polymer included in the polymerizable compositions.

The catalysts of contemplated polymerizable formulations can comprise a peroxide, platinum, tin, a combination thereof, or other suitable catalyst. An exemplary platinum catalyst for hydrosilylation reactions can comprise a complex of platinum with a vinyl siloxane acting as a ligand. An example of this is the Karstedt's catalyst. Other contemplated catalysts include, rhodium complex in vinly silicone fluid, organotin catalyst such as dibutyltin dilaurate, stannous octoate, dibutlytin diacetate, peroxide catalysts such as benzoyl peroxide, 2,4 dichlorobenzoyl peroxide, dicumyl peroxide, 2,5-dimethyl-2,5-di(tert-butylperoxy)hexane. In still further contemplated aspects, platinum may be replaced at least to some degree by other metals, including silver and copper, in nanoparticulate form or ionic form, which advantageously will also provide antimicrobial effect.

The catalyst can be present in the formulation in any suitable amount, for example, between 0.001-10 wt % (of the combined two part formulation where the catalyst and crosslinker are combined), more preferably between 0.01 and 1 wt %, and more preferably between 0.07 and 0.13 wt % (e.g., 0.1 wt %) of the polymerizable composition, and can include between 1-250 ppm, between 5-70 ppm, more preferably between 15-60 ppm (e.g., 30 ppm) of pure platinum. Notably, the amount of catalyst will affect the working time of the mixed composition, and higher quantities of catalyst will decrease the time required to seal a bleed. Thus, higher than normal (e.g., as recommended by manufacturer or published in the relevant art) quantities of catalyst are generally preferred.

The platinum catalyst will preferably be separated from the crosslinker until placed within, or on, the injury. Alternatively or additionally, the platinum catalyst can be combined with the crosslinker no more than 5 minutes, no more than 3 minutes, and preferably no more than 1 minute or 0.5 minute prior to being placed within, or on, the injury. Alternatively or additionally, the component or formulation comprising the platinum catalyst can be placed within the injury before or after the formulation or component comprising the crosslinker is placed within, or on, the injury. As discussed in more detail below, a base component (e.g., spray) comprising the same or different catalyst could be applied prior to any of the first formulation (including the platinum catalyst) and the second formulation (including the crosslinker). Therefore, contemporaneous application of the catalyst and the crosslinker by mixing the composition at the time of application is also contemplated.

Where a filler is included in the polymerizable formulation, an exemplary filler includes amorphous fumed silica having a surface area of between 100-300 $m^2$/gram (e.g., approximately 200 $m^2$/gram). Other contemplated fillers include fumed silica with low surface area (e.g., 100 $m^2$/gram), fumed silica with high surface area (e.g., 400 $m^2$/gram), precipitated silica, diatomaceous earth, titanium dioxide, zinc oxide, barium sulfate, colloidal silica, and boron nitride.

The filler can comprise between 0-80 wt %, more preferably between 5-35 wt % and even more preferably between 10-23 wt % (e.g., 16 wt %) of the combined two part formulation where the catalyst and crosslinker are combined. The surface of the silica can be treated with trimethyl silyl groups so that it is more soluble with the polymer.

A suitable thixotropic additive (e.g., a compound that reduces the flowability of a material rendering it non-slump)

can also be included in some contemplated polymerizable compositions in any suitable amount. For example, the thixotrope can comprise between 0.1-5 wt %, between 0.5-2.5 wt %, and more preferably between 1-2 wt % (e.g., 1.5 wt %) of the combined two part formulation where the catalyst and crosslinker are combined. An exemplary thixotrope included in some contemplated formulations is a hydroxyl endblocked polydimethyl siloxane with a chain length of between 10-20 repeating units (e.g., 15 repeating units with a molecular weight of 1100 Daltons). The hydroxyl groups on the polymer ends can react with the surface hydroxyl groups of the fumed silica causing the silica to become less flowable.

Suitable adhesion promoters can also be included in the polymerizable composition to increase the bond strength of the adhesive (polymerizable composition or seal) to the substrate (e.g., skin or injured tissue) as curing occurs. Tetrapropoxysilane is an exemplary adhesion promoter commonly used in silicone primers. Without wishing to be bound by any particular theory, the applicant contemplates that the reactive silane may form hydrogen or even covalent bonds with the skin or injured tissue, possibly catalyzed by heme, iron, and/or other components in blood. The adhesion promoter, when included in the polymerizable composition, can comprise between 0.01-10 wt %, between 0.1 and 5 wt %, and more preferably between 0.4 and 1.2 wt % (e.g., 0.8 wt %) of the polymerizable composition.

Additional adhesion promoters suitable for contemplated polymerizable formulations include those shown in Table 1, along with relevant results. In the below example, equal parts of the first and second components as described in Table 2 below including the different adhesion promoters were mixed and a thin layer was applied to a forearm and allowed to polymerize at room temperature. The samples were evaluated by recording the time that the edges began to lift from the skin. Once the edges lifted, the samples were peeled off and evaluated qualitatively for how difficult it was to peel completely off the skin. Each adhesion promoter was evaluated, and the results are described in Table 1 below. All percentages used herein are weight percentages (wt %) unless otherwise indicated.

TABLE 1

| Formulation | Edge Lifting Began | Adhesion to skin |
| --- | --- | --- |
| Formulation of table 2 with no adhesion promoter | 1 hour | poor |
| Formulation of table 2 with 1% Tetrapropoxysilane | 5 hours | good |
| Formulation of table 2 with 1.5% Tetrapropoxysilane | 5 hours | good |
| Formulation of table 2 with 1% 3-aminopropyltrimethoxysilane | 3.25 hours | good |
| Formulation of table 2 with 1.5% 3-aminopropyltrimethoxysilane | 3.25 hours | good |
| Formulation of table 2 with 1% Tris(2-methoxyethoxy)(vinyl)silane | 2 hours | poor |
| Formulation of table 2 with 1.5% Tris(2-methoxyethoxy)(vinyl)silane | 2.5 hours | poor |
| Formulation of table 2 with 1% Vinyltriethoxysilane | 2 hours | poor |
| Formulation of table 2 with 1.5% Vinyltriethoxysilane | 2.5 hours | poor |
| Formulation of table 2 with 1% Tetrakis(2-methoxyethyl)ester | 4 hours | good |
| Formulation of table 2 with 1% Tetrakis(2-methoxyethyl)ester | 4 hours | good |
| Formulation of table 2 with 1% Trimethoxy-7-octenylsilane | 5 hours | good |
| Formulation of table 2 with 1% Trimethoxy-7-octenylsilane | 5 hours | good |
| Formulation of table 2 with 0.25% N-(triethoxysilylpropyl)-O-polyethylene oxide urethane | 6.5 hours | good |
| Formulation of table 2 with 0.5% N-(triethoxysilylpropyl)-O-polyethylene oxide urethane | 6.5 hours | good |
| Formulation of table 2 with 0.25% N-(triethoxysilylpropyl)-O-polyethylene oxide urethane and 1.5% Tetrapropoxysilane | 18 hours | Excellent (synergistic effect with respect to adhesion where two adhesion promoters were used) |

The curable formulations used in each of the compositions of Table 1 are shown in Table 2. The adhesion promoter(s) of Table 1 were added to Part 2 of the formulation. However, it should be appreciated that the adhesion promoter could alternatively or additionally be added to Part 1 of the formulation. It should also be appreciated that the percentages shown in Part 2 below are modified once the adhesion promoter(s) are added.

TABLE 2

| Part 1 | | Part 2 | |
| --- | --- | --- | --- |
| Component | wt % | Component | wt % |
| Vinyl endblocked polydimethyl siloxane polymer | 79.95 ± 5 | Vinyl endblocked polydimethyl siloxane polymer | 76.985 ± 5 |
| Fumed silica with surface area of 200 m$^2$/gram | 19.99 ± 2 | Fumed silica with surface area of 200 m$^2$/gram | 19.2 ± 2 |
| Platinum catalyst complex | 0.06 ± .3 | Trimethyl endblocked methyl-hydrogen siloxane polymer crosslinker (containing 50% methyl hydrogen and 50% dimethyl) | 3.8 ± 1 |
| | | 1,3,5,7-tetramethyl-1,3,5,7-tetravinyl-cyclotetrasiloxane | 0.015 ± .005 |

It is also contemplated that inert pigments can be suspended in the polymerizable formulations without leaching into the wound or body. Suitable uses for inert pigments can include visibility, aesthetics (e.g., with designs) or camouflaging (e.g., flesh tones, bright tones, or any other suitable tones), or color-coding (e.g., red for laceration with lodged foreign particles, yellow for infected wound, etc.). Some contemplated powdered pigments can advantageously be broken down to a size of less than 20 microns, more preferably less than 15 microns to allow for even distribution or dispersion throughout the polymerizable formulation. Additionally or alternatively, concentrated liquid or gum color pigments can be added to one or more components of the polymerizable formulation.

Radio opaque or other particles (e.g., barium sulfate, zirconium dioxide) could be suspended or otherwise incorporated into the polymerizable formulations such that the cured seal can be detected by X-ray, computed tomography scans, ultrasound imaging or MRI scans. In some preferred embodiment, at least 8 wt %, more preferably at least 10 wt % (e.g., at least 11 wt %, between 8-50 wt %, between 10-20 wt %) is included in the combined two part polymerizable formulation for detection by X-ray. The radio opaque particles could be added to the polymerizable formulation in any suitable matter, and could even be pre-mixed with one or more of its components. For example, the radio opaque particles could be mixed in with the first formulation component, second formulation component, silicone polymer, platinum catalyst, crosslinker, adhesion promoter, cure inhibitor, filler, thixotropic agent, or any combination thereof. Alternatively, the particles could be added as a top layer to the composition while curing.

It is contemplated that the first and second formulations can react with each other at various temperatures, including for example at temperatures between −20 and 80 degrees Celsius, more typically between 0 and 60 degrees Celsius, and even more typically between 10 and 50 degrees Celsius. For example, it is contemplated that the formulations will be capable of reacting together to form a seal at room temperature (20±5° C.) and atmospheric pressure, or advantageously in the presence of a catalyst, by a hydrosilylation reaction or a condensation reaction, or a crosslinking reaction in the presence of a peroxide.

A complete seal can be formed within 20 minutes, within 10 minutes, more preferably within five minutes, within three minutes, within two minutes, or even within one minute. The seal can have any suitable thickness to treat or manage the injury, for example a thickness of between 0.1 mm and 50 mm, between 1 mm and 40 mm, between 1 mm and 20 mm, between 1 mm and 10 mm, or between 1 mm and 5 mm. Additionally, to stabilize a wound or otherwise distorted tissue, it should be appreciated that missing tissue volume can be replaced by contemplated cured compositions.

Upon full curing, the seal can have a hardness sufficient to prevent unwanted flowing of the seal. For example, the seal can have a hardness of at least 1, or at least 5, or at least 10 on the Shore 00 durometer scale, at least 1, or at least 5, or at least 10 on the Shore A scale, a hardness of between 0 on the Shore 00 durometer scale and 40 on the Shore A durometer scale, a hardness of between 10 on the Shore 00 durometer scale and 30 on the Shore A durometer scale, a hardness of between 15-25 on the Shore A durometer scale, or a hardness of between 18-22 on the Shore A durometer scale. The work time of the polymerizable composition can be approximately half of the cure time (e.g., about sixty seconds where the cure time is about two minutes).

Additionally or alternatively, the seal can have an elasticity that allows for movement and stretching of the body without compromising the seal or causing discomfort or pain. For example, some contemplated compositions will have an elasticity at break of at least 200%, more preferably at least 300%, and more preferably at least 400% (e.g., between 200-1000%, between 400 and 800%, between 450-600%). As used herein, the term "% elasticity at break" refers to the extension of a length of a cured seal from an unstretched and normal configuration before tearing, at room temperature, wherein the cured seal has a thickness of between 3-5 mm in the unstretched, normal configuration. For example, where a cured seal has an at least 180% elasticity at break, the cured seal, when normally having a thickness of between 3-5 mm, can be stretched to at least 180% of its length before tearing (e.g., from 10 mm to at least 18 mm before tearing). Viewed from a different perspective, the seal can have a tensile strength that allows significant force to be applied while maintaining its integrity (e.g., between 100-2000 psi, between 200-800 psi, between 400-650 psi).

In still further contemplated aspects, it should be noted that the compounds and compositions according to the inventive subject matter can also be used to affix non-tissue materials to a person, and particularly contemplated non-tissue materials include silicon sheds or gauze or other medically acceptable wound covers that have preferably been pretreated to so bond with the non-tissue materials. In the case of silicon sheets it should be appreciated that such sheets may be used as cover material that may or may not be applied under tension to so apply pressure to a treated wound. Advantageously, as the he compounds and compositions according to the inventive subject matter undergo polymerization silicon sheets are bonded to the compounds and compositions according to the inventive subject matter and may so further provide a protective cover or wrap above the injured and treated area. Moreover, it should be noted that medical tubing, and especially silicon tubing may be glued into place on a patient by simply applying a small portion of the compounds and compositions according to the inventive subject matter to the skin of a person, and by contacting the tubing with the compounds and compositions while they polymerize.

Moreover, and especially where the compounds and compositions according to the inventive subject matter are used as a cover and seal for a traumatic wound that includes fragments of ammunition, explosives, or other environmental debris, contemplated compounds and compositions may also be used to fix the debris in place to avoid further trauma. Where desirable, contemplated compounds and compositions may also at least partially engulf foreign objects, which can be removed after polymerization together with the cured materials.

Where a base component is applied to the injury, for example prior to applying the polymerizable composition that forms a seal, such base component could comprise at least one of an anesthetic, an antiseptic, an adhesion promoter, an antipruritic, a catalyst, a haemostatic agent, and a vasoconstrictor. Viewed from another perspective, the base component could advantageously provide one or more of a pain relieving, antimicrobial, or blood coagulative effect. Additionally or alternatively, the base component could act as or include a primer that promotes adhesion of the polymerizable composition to the skin or tissue when applied, and include a catalyst to decrease the cure time at the wound edges of the polymerizable composition. Preferably, the base component will not negatively impact the polymerizable composition's ability to adhere to the skin or tissue, or cure in situ in a short amount of time. Likewise, one or both components of polymerizable compositions may include at least one of an anesthetic, an antiseptic, an adhesion promoter, an antipruritic, a catalyst, a hemostatic agent, and a vasoconstrictor. Thus, polymerizable compounds and compositions could advantageously provide one or more of a pain relieving, antimicrobial, or blood coagulative effect.

Contemplated local anesthetics include, among others, xylocaine, lidocaine, lignocaine, bupivacaine, benzocaine, tetracaine (amethocaine), ropivacaine, prilocaine, procaine, cinchocaine, mepivacaine and etidocaine. Each local anesthetic (or the combination of anesthetics) can be present in the base component in any suitable amount. For example, it is contemplated that the local anesthetic can be present in a spray, ointment, jelly or other composition in any suitable concentration, including for example, a concentration of between 1-500 mg/ml, between 1-250 mg/ml, between 5-100 mg/ml, or between 5-50 mg/ml. If the local anesthetic (or other base ingredient) is included in the polymerizable composition, for example instead of or in addition to the base, it is contemplated that the same, lower or higher concentration of the local anesthetic could be included.

Contemplated antiseptics include benzalkonium chloride, tea tree oil, alcohol, hydrogen peroxide, iodine, and boric acid. Each antiseptic (or the combination of antiseptics) can be present in the base component in any suitable amount. For example, it is contemplated that the antiseptic can be present in the base (e.g., a spray, ointment, jelly, other composition) in any suitable concentration, including for example, a concentration of between 0.1-100 mg/ml, between 0.1-50 mg/ml, between 0.1-10 mg/ml, between 0.1-5 mg/ml, or between 0.8-1.8 mg/ml. Viewed from a different perspective, the antiseptic can be present in the base component at a concentration of between 0.01-1.0 w/w %, between 0.01-0.5 w/w %, or between 0.08-0.18 w/w %.

Contemplated adhesion promoters can include a silane coupling agent containing one or more functional groups that bond with the polymerizable composition or components thereof. Some contemplated adhesion promoters include a tetramethoxysilane, a tetraethoxysilane, a tetraisopropoxysilane, a tetrapropoxysilane, a tetrabutoxysilane, and a tetraacetoxysilane, a 3-aminopropyltrimethoxysilane, tris(2-methoxyethoxy)(vinyl)silane, vinyltriethoxysilane, tetrakis(2-methoxyethyl)ester, and trimethoxy-7-octenylsilane.

When included, the adhesion promoter(s) can be present in the base component in any suitable amount. For example, it is contemplated that the adhesion promoter can be present in a spray, ointment, jelly or other composition in any suitable concentration, including for example, a concentration of between 0.1-100 mg/ml, between 0.1-75 mg/ml, between 0.1-50 mg/ml, between 0.1-10 mg/ml, or between 0.5-10 mg/ml.

Vasoconstrictors can be included in contemplated base compositions, and can have several beneficial effects, for example, when added to a local anesthetic. For example, the vasoconstrictor can decrease the peak plasma concentration of the local anesthetic agent, increase the duration and quality of the anesthesia, reduce the minimum concentration of anesthetic needed for nerve blocking, and decrease the amount of blood lost. Contemplated vasoconstrictors include epinephrine, norepinephrine, vasopressin, oxymetazoline, phenylephrine, anhydrous aluminum sulfate, and pseudoephedrine.

When included, the vasoconstrictor(s) can be present in the base component in any suitable amount. For example, it is contemplated that the vasoconstrictor can be present in a spray, ointment, jelly or other composition in any suitable concentration, including for example, a concentration of between 0.1-100 mg/ml, between 0.1-75 mg/ml, between 0.1-50 mg/ml, between 0.1-10 mg/ml, or between 0.5-10 mg/ml.

All suitable antipuritic components are contemplated, and can include antihistamines such as diphenhydramine, corticosteroids such as hydrocortisone, methol, camphor, or a local anesthetic (e.g., lidocaine, pramoxine, benzocaine). When included, the antipuritic component(s) can be present in the base component in any suitable amount. For example, it is contemplated that the antipuritic can be present in a spray, ointment, jelly or other composition in any suitable concentration, including for example, a concentration of between 1-500 mg/ml (0.1-50%), between 1-100 mg/ml (0.1-10%), or between 1-50 mg/ml (0.1-5%).

A haemostatic agent could also be included in contemplated base components or polymerizable compounds and compositions to slow down or stop a bleed when applied directly on the source. Some exemplary haemostatic agents include antifibrinolytics, blood coagulation factors, fibrinogen, vitamin K, microfibrillar collagen hemostat (MCH), chitosan hemostats, nitric oxide donors and nitric oxide releasing compositions (e.g. sodium nitroprusside, NONO-NSAIDs, see e.g., *Toxicol Appl Pharmacol.* 2012 Oct. 15; 264(2): 161-166) and thromboplastin.

Similarly to the polymerizable composition, the base component can also include a silicone or other catalyst that promotes curing of the polymerizable composition, which can be present in any suitable concentration (e.g., between 0.001-50 mg/ml).

Where the base component is a silicone primer, the primer will typically include one or more reactive silanes, a catalyst, and a solvent carrier (among other things). The reactive silanes can include a reactive group that is compatible with the polymerizable composition, and another reactive group that is compatible with the substrate (e.g., skin, tissue) to thereby promote adhesion of the polymerizable composition to the substrate. One exemplary silicone primer comprises between 88-93 wt % isopropyl alcohol (e.g., 88 wt %), between 1-5 wt % tetrapropoxy silane (e.g., 3%), between 1-5 wt % titanium IV butoxide (e.g., 3%), and between 0.01-2 wt % platinum catalyst (e.g., 1 wt %). However, all suitable silicone primer compositions are contemplated.

The PHOSITA should appreciate that different materials can be obtained from different commercial suppliers. For example, it is contemplated that components of some contemplated polymerizable compositions or base component can be obtained from commercial suppliers, for example, Silbond Corporation, Chemat, H.W. Sands Corp., Fluorochem USA, Gelest, Inc., Dupont Performance chemicals, Nusil Technology, Power Chemical Corporation, Rhodia Silicones, Reliance Silicones, or Zentek.

Further additives suitable with the polymerizable compounds and compositions include one or more functional ingredients, and especially antibiotics (e.g., beta lactam antibiotics, tetracycline type antibiotics, (nanoparticulate) silver and/or copper, boric acid, etc.), antifungals, analgesics, antineoplastic agents, antivirals, sedatives, hypnotics, cytokines, chemokines, growth factors, hormones, nitric oxide donor/precursor compounds, and/or sunscreen/UV absorbing agents. On the other hand, non-functional ingredients include one or more colorants, perfumes, flavors, etc. Still further, micro RFID chips or tags may be included on which patient history and/or prior treatment may be recorded to generate a chain of record.

In still further contemplated uses, the compounds and compositions of the inventive subject matter may be used to temporarily glue down silicon and/or other compression strips/tapes and tubing to the wound and/or skin of a patient. Likewise, it should be noted that partially or completely detached skin flaps could be glued onto the wound to secure the tissue in place until proper treatment can be administered. Moreover, the compounds and compositions of the inventive subject matter may also be used to temporarily seal/close off the outer or inner ear canal or a nostril, or be employed in dental uses. For example, periodontal treatment may be done with antimicrobial agents, growth factors, or the compounds and compositions of the inventive subject matter may be used as temporary sealant after tooth extraction. Moreover, the compounds and compositions of the inventive subject matter may be used in combination with other therapies, and especially light based therapies.

In further examples, contemplated compounds and compositions can be used in the treatment of cancer. Among other suitable options, the polymerizable compounds can be used for tumor embolization, for delivery of timed released cancer drugs to tumor (e.g., encapsulation with polymerizable compounds using slow release of a drug, or for skin or cervical cancer to protect the cancer and deliver locally drugs to the tumor cells), for visualization of a tumor. Still further uses include cervical cancer treatment where compounds are formed as a cervical cap with cancer medication released from the material, which can be easily applied and removed. Likewise, contemplated compounds and compositions can be applied to penile dysphasia, penile cancer, penile warts, urethral cancer or dysphasia, tear duct cancer.

Still further contemplated uses include treatment of nail avulsion, abscesses after incision and drainage (e.g., to kill infection and provide pain relief). Likewise, sinuses and fissures can be drained and the polymerizable compounds can be added to treat infected fissures and sinuses in the body.

Additionally, it is contemplated that the compositions and methods can be used as thin skin suturing bolster and to minimize tension on wound edges, leading to better cosmesis. For example elderly, neonates have thin skin, where the compounds and compositions can be applied topically and act like a skin thickening agent.

Additionally contemplated topical uses of contemplated compounds and compositions include use as a band-aid that is applied in liquid form and then polymerizes, with will be less painful upon removal than ordinary band-aids, as a "second skin" burn-healing product, with anti-microbials added, to speed healing and to protect burns from abrasion and painful air exposure, use on intact blister to press blister back down to allow fluid to reabsorb, and on open blisters, insect stings, as well as animal bites. Contemplated compounds and compositions can also be used as a treatment/camouflage for cold sores, or as a treatment/pain control and camouflage for Shingles (Herpes Zoster), herpes of the face and lips.

Furthermore, it is contemplated that the contemplated compounds and compositions can be used as a sealant on wounds from any medical device that pierces skin, for example, to prevent contamination, leakage of air and/or body fluids, or in conjunction with a chest tube, ileostomy bag, urinary catheter, or any device or tube that is entering the body (can be placed around entry point of chest tube or other into the body where sutures are placed to anchor the tube in skin) to decrease infection.

Additionally it should be noted that amputated body parts and even limbs can be encased in contemplated compounds and compositions to keep it protected and moist.

EXAMPLES

Table 3 shows an exemplary two part polymerizable formulation having a dual adhesion promoter system. In this case, the two adhesion promoters work synergistically to increase adhesion to skin (or tissue) when compared to formulations having only one of the adhesion promoters. Without wishing to be bound by any particular theory, Applicant contemplates that one adhesion promoter makes the second more available at the surface of the formulation. Although the two adhesion promoters in this example are provided in Part 2 of the formulation, it should be appreciated that one adhesion promoter could be provided in each of Parts 1 and 2, that both adhesion promoters could be provided in Part 1, or that one adhesion promoter could be provided in the polymerizable formulations while a second adhesion promoter is provided in a base component.

The exemplary formulation of Table 3 is compounded to provide a short working and setting time. Specifically, the formulation has a working time of between 20-40 seconds (typically about 30 seconds), and a setting time of between 4-6 minutes (typically about 5 minutes) when Part 1 and Part 2 are mixed together and placed on skin.

TABLE 3

| Part 1 | | Part 2 | |
|---|---|---|---|
| Component | wt % | Component | wt % |
| Vinyl endblocked polydimethyl siloxane polymer (chain length 350 repeating units) | 79.947 | Vinyl endblocked polydimethyl siloxane polymer (chain length 350 repeating units) | 74-75 |
| Fumed silica with surface area of 200 $m^2$/gram | 19.91 | Fumed silica with surface area of 200 $m^2$/gram | 18.5-19 |
| Platinum catalyst complex | 0.143 | Trimethyl endblocked methyl-hydrogen siloxane polymer crosslinker (containing 50 wt % methyl hydrogen and 50 wt % dimethyl) | 3.5-4.0 |
| | | 1,3,5,7-tetramethyl-1,3,5,7-tetravinyl-cyclotetrasiloxane | 0.013-0.017 |

TABLE 3-continued

| Part 1 | | Part 2 | |
|---|---|---|---|
| Component | wt % | Component | wt % |
| | | Tetrapropoxysilane adhesion promoter | 2.2-28 |
| | | N-(triethoxysilylpropyl)-O-polyethylene oxide urethane adhesion promoter | 0.37-0.45 |

It is also contemplated that the components shown in Table 1 could be included in Part 1 and Part 2 of the formulation in different concentration ranges as set forth below in the example of Table 4 achieving a desirable range of similar working times (e.g., between 10-120 seconds), similar setting times (e.g., between 1-10 minutes), similar adhesion properties (as described in Table 1), hardness of between 5-80 on the Shore A hardness scale, tensile strength between 200-1500 psi, and elasticities at break (of between 200-1000%).

TABLE 4

| Part 1 | | Part 2 | |
|---|---|---|---|
| Component | wt % | Component | wt % |
| Vinyl endblocked polydimethyl siloxane polymer (100-1000 DP) | 60-90 | Vinyl endblocked polydimethyl siloxane polymer (100-1000 repeating siloxy units) | 60-90 |
| Fumed silica with surface area of 200 m$^2$/gram (100-400 m$^2$/gram) | 10-30 | Fumed silica with surface area of 200 m$^2$/gram | 10-30 |
| Platinum catalyst complex | 0.06-0.2 | Trimethyl endblocked methyl-hydrogen siloxane polymer crosslinker (containing 50% methyl hydrogen and 50% dimethyl) | 2-10 |
| | | 1,3,5,7-tetramethyl-1,3,5,7-tetravinyl-cyclotetrasiloxane | .001-.05 |
| | | Tetrapropoxysilane adhesion promoter | 1-5 |
| | | N-(triethoxysilylpropyl)-O-polyethylene oxide urethane adhesion promoter | 0.1-2 |

Where specific additives are contemplated, it should be noted that these can be added in a simple manner to Part1, Part2, or both Parts as exemplarily shown in Table 5. In this exemplary formulation, barium sulfate is added as an imaging contrast agent, which is contemplated to have comparable work times (e.g., between 10-120 seconds), setting times (e.g., between 1-10 minutes), adhesion properties, hardness, tensile strength, and elasticities at break as the formulation of Table 1.

TABLE 5

| Part 1 | | Part 2 | |
|---|---|---|---|
| Component | wt % | Component | wt % |
| Vinyl endblocked polydimethyl siloxane polymer | 66.6 ± 20 | Vinyl endblocked polydimethyl siloxane polymer | 74.9 ± 20 |
| Fumed silica with surface area of 200 m$^2$/gram | 16.7 ± 10 | Fumed silica with surface area of 200 m$^2$/gram | 18.7 ± 10 |

TABLE 5-continued

| Part 1 | | Part 2 | |
|---|---|---|---|
| Component | wt % | Component | wt % |
| Platinum catalyst complex | 0.05 (0.001-0.2) | Trimethyl endblocked methyl-hydrogen siloxane polymer crosslinker (containing 50% methyl hydrogen and 50% dimethyl) | 3.7 ± 3 |
| Barium Sulfate (to make the formulation radio-opaque) | 16.7 ± 15 | 1,3,5,7-tetramethyl-1,3,5,7-tetravinyl-cyclotetrasiloxane | 0.015 (between 0.001-0.05) |
| | | Tetrapropoxysilane adhesion promoter | 2.2 ± 2 |
| | | N-(triethoxysilylpropyl)-O-polyethylene oxide urethane adhesion promoter | 0.37 (0.1-2) |

Table 6 shows yet another exemplary formulation including one or more pigments, which is contemplated to have comparable work times (e.g., between 10-90 seconds), setting times (e.g., between 1-10 minutes), adhesion properties, and elasticities at break as the formulation of Table 1.

TABLE 6

| Part 1 | | Part 2 | |
|---|---|---|---|
| Component | wt % | Component | wt % |
| Vinyl endblocked polydimethyl siloxane polymer | 78.4 ± 20 | Vinyl endblocked polydimethyl siloxane polymer | 74.9 ± 20 |
| Fumed silica with surface area of 200 m$^2$/gram | 19.6 ± 10 | Fumed silica with surface area of 200 m$^2$/gram | 18.7 ± 10 |
| Platinum catalyst complex | 0.06 (0.001-0.2) | Trimethyl endblocked methyl-hydrogen siloxane polymer crosslinker (containing 50% methyl hydrogen and 50% dimethyl) | 3.7 ± 3 |
| Pigment (e.g., yellow, orange, green, blue, brown) | 1.96 ± 1.5 | 1,3,5,7-tetramethyl-1,3,5,7-tetravinyl-cyclo-tetrasiloxane | 0.015 (between 0.001-0.05) |
| | | Tetrapropoxysilane adhesion promoter | 2.2 ± 2 |
| | | N-(triethoxysilylpropyl)-O-polyethylene oxide urethane adhesion promoter | 0.37 (0.1-2) |

Tables 7-10 show further exemplary formulations only including one adhesion promoter, which is contemplated to have comparable work times (e.g., between 10-90 seconds), setting times (e.g., between 1-10 minutes), hardness, tensile strength, and elasticities at break as the formulation of Table 1, but a lower adhesion strength to skin likely due to a lack of synergistic effect with a second adhesion promoter.

TABLE 7

| Part 1 | | Part 2 | |
|---|---|---|---|
| Component | wt % | Component | wt % |
| Vinyl endblocked polydimethyl siloxane polymer | 79.95 ± 20 | Vinyl endblocked polydimethyl siloxane polymer | 75.29 ± 20 |
| Fumed silica with surface area of 200 m$^2$/gram | 19.99 ± 10 | Fumed silica with surface area of 200 m$^2$/gram | 18.8 ± 10 |

TABLE 7-continued

| Part 1 | | Part 2 | |
|---|---|---|---|
| Component | wt % | Component | wt % |
| Platinum catalyst complex | 0.06 (0.001-0.2) | Trimethyl endblocked methyl-hydrogen siloxane polymer crosslinker (containing 50% methyl hydrogen and 50% dimethyl) | 3.8 ± 3 |
| | | 1,3,5,7-tetramethyl-1,3,5,7-tetravinyl-cyclotetrasiloxane | 0.015 (between 0.001-0.05) |
| | | Tetrapropoxysilane adhesion promoter | 2.3 ± 2 |
| | | | 15 |

TABLE 8

| Part 1 | | Part 2 | |
|---|---|---|---|
| Component | wt % | Component | wt % |
| Vinyl endblocked polydimethyl siloxane polymer | 79.95 ± 20 | Vinyl endblocked polydimethyl siloxane polymer | 75.29 ± 20 |
| Fumed silica with surface area of 200 $m^2$/gram | 19.99 ± 10 | Fumed silica with surface area of 200 $m^2$/gram | 18.8 ± 10 |
| Platinum catalyst complex | 0.06 (0.001-0.2) | Trimethyl endblocked methyl-hydrogen siloxane polymer crosslinker (containing 50% methyl hydrogen and 50% dimethyl) | 3.8 ± 3 |
| | | 1,3,5,7-tetramethyl-1,3,5,7-tetravinyl-cyclotetrasiloxane | 0.015 (between 0.001-0.05) |
| | | N-(triethoxysilylpropyl)-O-polyethylene oxide urethane adhesion promoter | 0.37 (0.1-2) |

TABLE 9

| Part 1 | | Part 2 | |
|---|---|---|---|
| Component | wt % | Component | wt % |
| Vinyl endblocked polydimethyl siloxane polymer | 79.95 ± 20 | Vinyl endblocked polydimethyl siloxane polymer | 75.29 ± 20 |
| Fumed silica with surface area of 200 $m^2$/gram | 19.99 ± 10 | Fumed silica with surface area of 200 $m^2$/gram | 18.8 ± 10 |
| Platinum catalyst complex | 0.06 (0.001-0.2) | Trimethyl endblocked methyl-hydrogen siloxane polymer crosslinker (containing 50% methyl hydrogen and 50% dimethyl) | 3.8 ± 3 |
| | | 1,3,5,7-tetramethyl-1,3,5,7-tetravinyl-cyclotetrasiloxane | 0.015 (between 0.001-0.05) |
| | | Tetrapropoxysilane adhesion promoter | 2.57 ± 2.5 |

TABLE 10

| Part 1 | | Part 2 | |
|---|---|---|---|
| Component | wt % | Component | wt % |
| Vinyl endblocked polydimethyl siloxane polymer | 79.95 ± 20 | Vinyl endblocked polydimethyl siloxane polymer | 75.29 ± 20 |
| Fumed silica with surface area of 200 m²/gram | 19.99 ± 10 | Fumed silica with surface area of 200 m²/gram | 18.8 ± 10 |
| Platinum catalyst complex | 0.06 (0.001-0.2) | Trimethyl endblocked methyl-hydrogen siloxane polymer crosslinker (containing 50% methyl hydrogen and 50% dimethyl) | 3.8 ± 3 |
| | | 1,3,5,7-tetramethyl-1,3,5,7-tetravinyl-cyclotetra-siloxane | 0.015 (between 0.001-0.05) |
| | | N-(triethoxysilylpropyl)-O-polyethylene oxide urethane adhesion promoter | 2.57 ± 2.5 |

Table 11 shows a further exemplary formulation that includes a thixotropic agent added at a concentration of between 0.25-3 wt % to make the formulation non-slump. The formulation of Table 11 is contemplated to have comparable work times (e.g., between 10-90 seconds), setting times (e.g., between 1-10 minutes), adhesion properties, hardness, tensile strength, and elasticities at break as the formulation of Table 1.

TABLE 11

| Part 1 | | Part 2 | |
|---|---|---|---|
| Component | wt % | Component | wt % |
| Vinyl endblocked polydimethyl siloxane polymer | 79.32 ± 20 | Vinyl endblocked polydimethyl siloxane polymer | 74.9 ± 20 |
| Fumed silica with surface area of 200 m²/gram | 19.83 ± 10 | Fumed silica with surface area of 200 m²/gram | 18.7 ± 10 |
| Platinum catalyst complex | 0.06 (0.001-0.2) | Trimethyl endblocked methyl-hydrogen siloxane polymer crosslinker (containing 50% methyl hydrogenand 50% dimethyl) | 3.7 ± 3 |
| Hydroxyl endblocked polydimethyl siloxane (thixotrope) | 0.79 (between 0.25-3) | 1,3,5,7-tetramethyl-1,3,5,7-tetravinyl-cyclotetrasiloxane | 0.015 (between 0.001-0.05) |
| | | Tetrapropoxysilane adhesion promoter | 2.2 ± 2 |
| | | N-(triethoxysilylpropyl)-O-polyethylene oxide urethane adhesion promoter | 0.37 (0.1-2) |

Table 12 shows yet another exemplary formulation including less platinum catalyst than the formulation of Table 1, which is contemplated to require a longer cure time.

TABLE 12

| Part 1 | | Part 2 | |
|---|---|---|---|
| Component | wt % | Component | wt % |
| Vinyl endblocked polydimethyl siloxane polymer | 79.97 ± 20 | Vinyl endblocked polydimethyl siloxane polymer | 74.9 ± 20 |
| Fumed silica with surface area of 200 m²/gram | 19.99 ± 10 | Fumed silica with surface area of 200 m²/gram | 18.7 ± 10 |

TABLE 12-continued

| Part 1 | | Part 2 | |
|---|---|---|---|
| Component | wt % | Component | wt % |
| Platinum catalyst complex | 0.04 (0.001-0.2) | Trimethyl endblocked methyl-hydrogen siloxane polymer crosslinker (containing 50% methyl hydrogen and 50% dimethyl) | 3.7 ± 3 |
| | | 1,3,5,7-tetramethyl-1,3,5,7-tetravinyl-cyclotetrasiloxane | 0.015 (between 0.001-0.05) |
| | | Tetrapropoxysilane adhesion promoter | 2.2 ± 2 |
| | | N-(triethoxysilylpropyl)-O-polyethylene oxide urethane adhesion promoter | 0.37 (0.1-2) |

Table 13 shows further exemplary formulation including less crosslinker than the formulation of Table 1, which is contemplated to require a longer cure time.

TABLE 13

| Part 1 | | Part 2 | |
|---|---|---|---|
| Component | wt % | Component | wt % |
| Vinyl endblocked polydimethyl siloxane polymer | 79.95 ± 20 | Vinyl endblocked polydimethyl siloxane polymer | 76 ± 20 |
| Fumed silica with surface area of 200 $m^2$/gram | 19.997 ± 10 | Fumed silica with surface area of 200 $m^2$/gram | 79 ± 10 |
| Platinum catalyst complex | 0.06 (0.001-0.2) | Trimethyl endblocked methyl-hydrogen siloxane polymer crosslinker (containing 50% methyl hydrogen and 50% dimethyl) | 2.3 ± 2 |
| | | 1,3,5,7-tetramethyl-1,3,5,7-tetravinyl-cyclotetrasiloxane | 0.015 (between 0.001-0.05) |
| | | Tetrapropoxysilane adhesion promoter | 2.3 ± 2 |
| | | N-(triethoxysilylpropyl)-O-polyethylene oxide urethane adhesion promoter | 0.38 (0.1-2) |

Table 14 shows another exemplary formulation including no fumed silica.

TABLE 14

| Part 1 | | Part 2 | |
|---|---|---|---|
| Component | wt % | Component | wt % |
| Vinyl endblocked polydimethyl siloxane polymer | 99.93 | Vinyl endblocked polydimethyl siloxane polymer | 92.1 ± 20 |
| Platinum catalyst complex | 0.07 (0.001-0.2) | Trimethyl endblocked methyl-hydrogen siloxane polymer crosslinker (containing 50% methyl hydrogen and 50% dimethyl) | 4.6 ± 4 |
| | | 1,3,5,7-tetramethyl-1,3,5,7-tetravinyl-cyclotetrasiloxane | 0.018 (between 0.001-0.05) |
| | | Tetrapropoxysilane adhesion promoter | 2.8 ± 2 |

TABLE 14-continued

| Part 1 | | Part 2 | |
|---|---|---|---|
| Component | wt % | Component | wt % |
| | | N-(triethoxysilylpropyl)-O-polyethylene oxide urethane adhesion promoter | 0.46 (0.1-2) |

FIGS. 1-3B illustrate exemplary uses of some of the formulations listed in Tables 1-14 being tested in a laboratory in the presence of blood, platelet-rich plasma (PRP), and tissue. In FIG. 1, platelet-rich plasma (PRP) is prepared using a Harvest® processing system. The PRP was placed in a vacutainer tubes along with polymerizable formulations of the inventive subject matter, and a stick to facilitate removal upon curing. FIGS. 2A-32B illustrate the same compositions polymerized in the presence of blood, establishing that the polymerizable formulations are able to cure in the presence of blood. In these examples, the total cure time for the polymerizable formulations ranged from about 90 seconds to about five minutes.

Figure 3A:
FIGS. 3A-3B illustrate the polymerizable formulations after they have cured on a sample of meat (3A) and after the cured formulation has been removed from the meat sample (3B).
Figure 3B:
Figure 4:
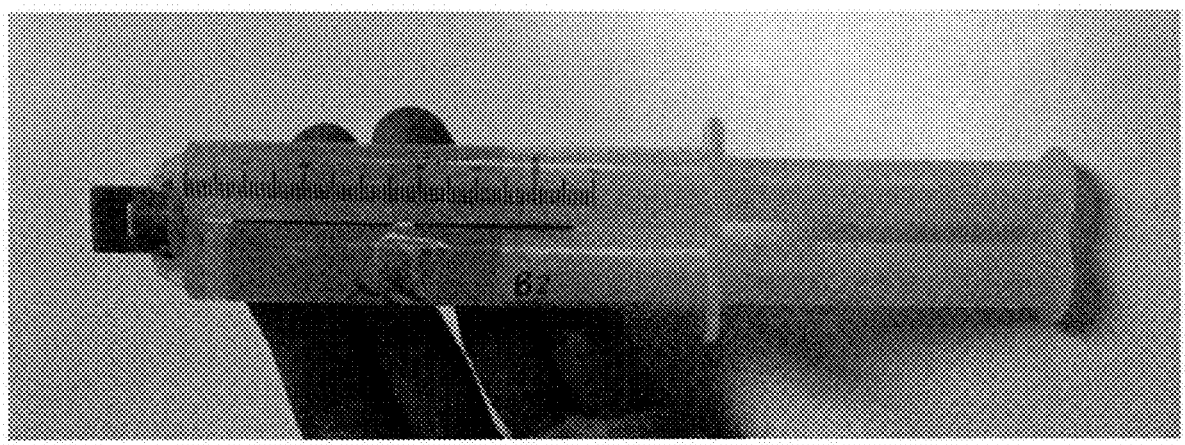
FIG. 4 illustrates a dual syringe that was used to store and dispense exemplary polymerizable formulations.

In FIGS. 3A and 3B, a polymerizable formulation was placed on a piece of raw meat and was found to fully cure in less than about three minutes. Notably, as can be seen in FIG. 3B, the cured composition was removable as a single piece, and was found to infuse approximately 0.25 mm-5 mm into crevaces of the tissue. FIG. 4 depicts an exemplary syringe-type device in which first and second components are kept separately prior to mixing in a nozzle through which the mixed composition is applied into a wound or injured area. Of course, it should be appreciated that numerous other application devices are also deemed suitable, and especially devices that keep first and second components separate until use. Thus, suitable devices will include rigid (tanks, cylinders, cans, etc.) or flexible containers (pouches, bags, etc.) that are fluidly coupled to each other to allow combination of at leas a portion of the contents of one container with the contents of the other. For example, a syringe type allows for multiple uses. On the other hand, single use devices are also contemplated in which, for example, a frangible seal separates two compartments with first and second components, wherein the seal can be broken to so allow mixing of the entire contents. Delivery of the mixed contents can then be performed through a separate nozzle.

Figure 5:
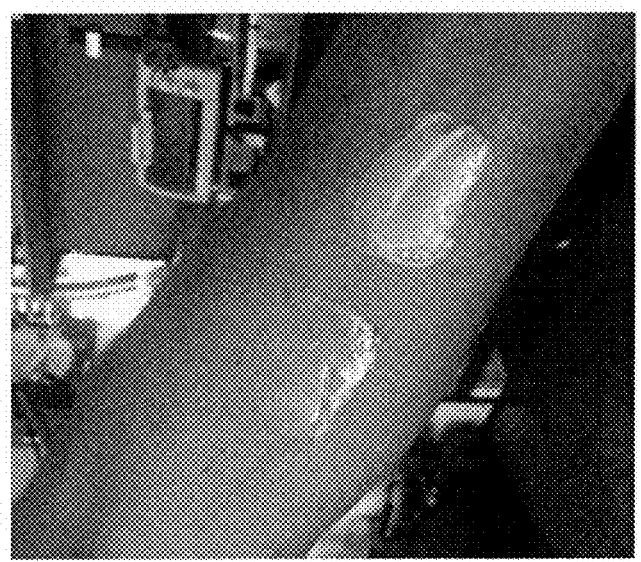
FIG. 5 illustrates a polymerizable formulation attached to skin including a yellow pigment.

FIG. 5 exemplarily illustrates contemplated compounds in combination with a dye. Here, it should be noted that the composition after polymerization adheres to the skin and is clearly visible as a colored flexible composition. Of course, it should be appreciated that the dye can be replaced with UV absorbing compounds for a sunscreen film that is waterproof and will not detach unless a user peels it off. Likewise, the dye in such films can also be replaced by a therapeutic entity (e.g., drug, botanical, etc.) for a desired therapeutic and/or cosmetic effect. For example, such film may be placed on a burn, a scar, a viral blister, an ulcer, an abrasion, an open or serum-filled blister (e.g., due to friction), and may remain for hours, and more typically days (e.g., at least 1 day, between 2-4 days, between 2-6 days, or even longer).

Figure 6A:
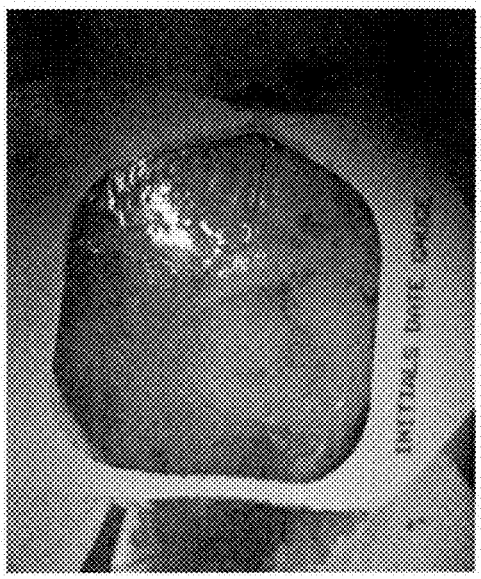
FIGS. 6A-6B illustrate a polymerizable formulation under a transparent cover placed within a wound (6A), and the cured seal after being peeled off the wound (6B).
Figure 6B:
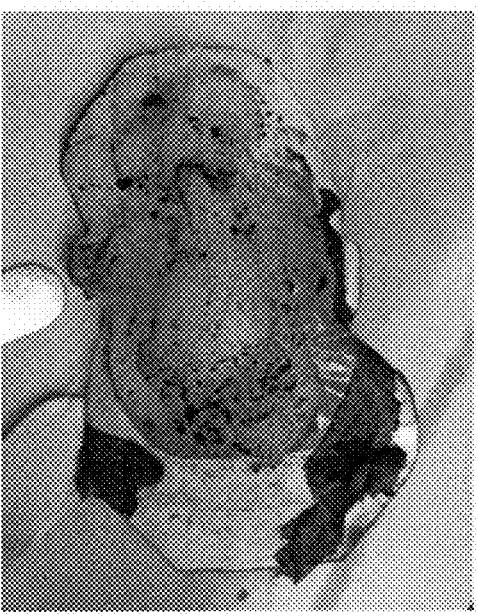
Figure 7A:
FIGS. 7A-7B illustrate a wound being sealed by a polymerizable formulation before complete curing (7A), and the fully cured seal after being peeled off the wound (7B).
Figure 7B:
Figure 8A:
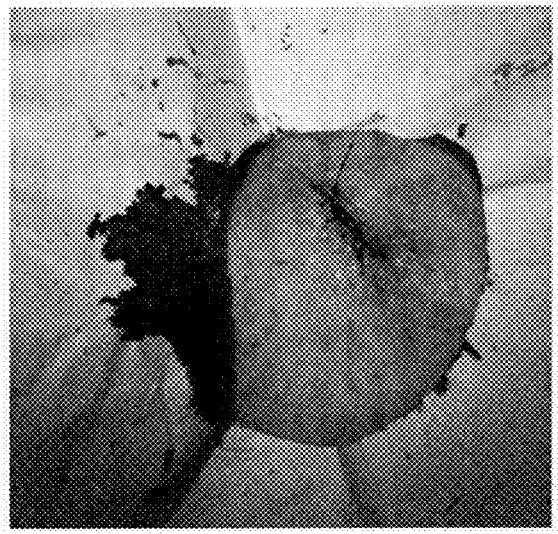
FIGS. 8A-8B illustrate a wound being sutured (8A), and a polymerizable formulation being placed over the sutured wound (8B).
Figure 8B:
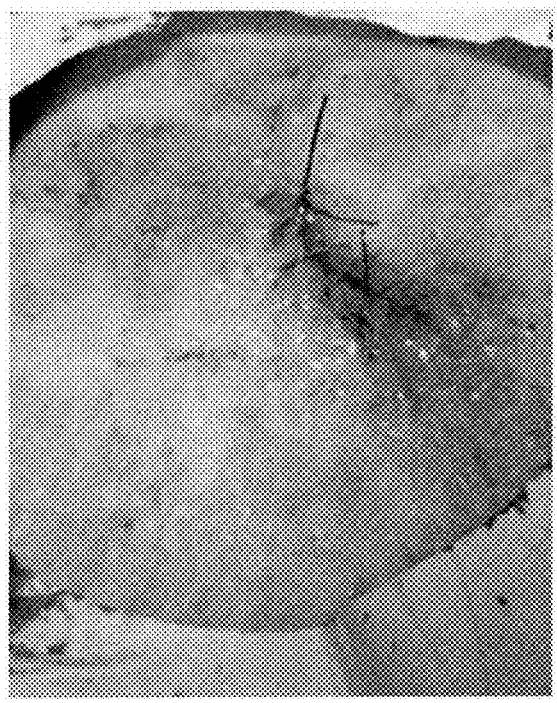

FIG. 6A illustrates placement of the polymerizable formulation within a wound (with cover placed above the formulation), and FIG. 6B shows the cured seal after being peeled off the wound. FIG. 7A illustrates a wound being sealed by a polymerizable formulation, FIG. 7B shows the seal after full polymerization and being peeled off the wound. FIGS. 8A-8B shows a wound being sutured, and a polymerizable formulation being placed over the sutured wound. In this use, applicant surprisingly discovered that the cured seal above the sutured wound had some properties stronger than skin, as a suture would not pull through the cured seal with the same strength applied to pull a suture through skin. More notably, for all human having wounds treated with polymerizable formulations of the inventive subject matter, cauterization was not required to stop a bleed, thereby reducing the amount of tissue damage caused.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Also, as used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. Moreover, and unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

The discussion herein provides example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

It should be apparent, however, to those skilled in the art that many more modifications besides those already described are possible without departing from the inventive concepts herein. The inventive subject matter, therefore, is not to be restricted except in the spirit of the disclosure. One skilled in the art will recognize many methods and materials similar or equivalent to those described herein, which could be used in the practice of the present invention. Indeed, the present invention is in no way limited to the methods and materials described.

Moreover, in interpreting the disclosure all terms should be interpreted in the broadest possible manner consistent with the context. In particular the terms "comprises" and "comprising" should be interpreted as referring to the elements, components, or steps in a non-exclusive manner, indicating that the referenced elements, components, or steps can be present, or utilized, or combined with other elements, components, or steps that are not expressly referenced.

What is claimed is:

1. A method for affixing a non-tissue material to skin of a person, comprising:
    applying a polymerizable composition to the skin of the person;
    contacting the polymerizable composition with the non-tissue material while the polymerizable composition polymerizes to so affix the non-tissue material to the skin;
    wherein the polymerizable composition comprises a silicone mixture, and wherein the silicone mixture comprises
        (a) a vinyl end-blocked polydimethylsiloxane as a first silicone elastomer component and a platinum catalyst, and
        (b) a vinyl end-blocked polydimethylsiloxane as a second silicone elastomer component and a trimethyl end-blocked methyl-hydrogen siloxane polymer as a silicone crosslinker; and
        (c) wherein the polymerizable composition comprises a first and a second adhesion promoter that synergistically enhance adhesion of the polymerized composition to the skin, and wherein the first and second adhesion promoter are N-(triethoxysilylpropyl)-O-polyethylene oxide urethane and tetrapropoxysilane.

2. The method of claim 1 wherein the non-tissue material is selected from the group
    consisting of a silicon sheet, medical tubing, silicon tubing, cloth, gauze, and a medically acceptable wound cover.

3. The method of claim 1 wherein the non-tissue material is pretreated to facilitate bonding of the non-tissue material.

4. The method of claim 1 wherein the polymerizable composition polymerizes in the presence of blood.

5. The method of claim 1 wherein the polymerizable composition forms an elastic seal upon polymerization.

6. The method of claim 5 wherein the seal is removable.

7. The method of claim 1 wherein the polymerizable composition polymerizes within two minutes.

8. The method of claim 1, wherein the silicone mixture has a work time of between 30-90 seconds and a cure time of between 1-5 minutes.

9. The method of claim 1, wherein the first and second adhesion promoter allow for adhesion of the polymerized composition to the skin over a period of at least 10 hours.

10. The method of claim 1, wherein the composition further comprises at least one of an antiseptic, fumed amorphous silica, and a thixotropic agent.

11. A polymerizable composition, comprising:
    a silicone mixture, wherein the silicone mixture comprises
        (a) a vinyl end-blocked polydimethylsiloxane as a first silicone elastomer component and a platinum catalyst, and
        (b) a vinyl end-blocked polydimethylsiloxane as a second silicone elastomer component and a trimethyl end-blocked methyl-hydrogen siloxane polymer as a silicone crosslinker; and
        (c) wherein the polymerizable composition further comprises a first and a second adhesion promoter that synergistically enhance adhesion of the polymerized composition to skin, and wherein the first and second adhesion promoter are N-(triethoxysilylpropyl)-O-polyethylene oxide urethane and tetrapropoxysilane.

12. The composition of claim 11, wherein the silicone mixture has a work time of between 30-90 seconds and a cure time of between 1-5 minutes.

13. The composition of claim 11, wherein the composition is formulated to adhere, upon polymerization, to skin over a period of at least 10 hours.

14. The composition of claim 11, further comprising at least one of an antiseptic, an antibacterial agent, an analgesic agent, a vasoconstrictor, fumed amorphous silica, and a thixotropic agent.

15. The composition of claim 11, wherein the composition polymerizes to form a seal having a hardness of between 0 on the Shore 00 durometer scale and 40 on the Shore A durometer scale.

16. The composition of claim 11, wherein the composition polymerizes to form a seal having a hardness of between 10 on the Shore 00 durometer scale and 30 on the Shore A durometer scale.

17. The composition of claim 11, wherein the composition polymerizes to form a seal having a hardness of between 15-25 on the Shore A durometer scale.

18. The composition of claim 11, wherein the composition polymerizes to form a seal having an elongation at break of between 200-800%.

19. The composition of claim 11, wherein the composition polymerizes to form a seal having a tensile strength of between 100-2000 psi.

20. The composition of claim 11, wherein the vinyl end-blocked polydimethylsiloxane and the platinum catalyst are enclosed in a first container, wherein the vinyl end-blocked polydimethylsiloxane and the trimethyl end-blocked methyl-hydrogen siloxane polymer are enclosed in a second container that is separate from the first container.

* * * * *